United States Patent [19]

Mitani et al.

[11] 4,355,645

[45] Oct. 26, 1982

[54] DEVICE FOR DISPLAYING MASTICATORY MUSCLE ACTIVITIES

[75] Inventors: Haruyasu Mitani, Kyoto; Eiko Mushimoto, Osaka, both of Japan

[73] Assignee: Kabushiki Kaisha Morita Seisakusho, Kyoto, Japan

[21] Appl. No.: 86,052

[22] Filed: Oct. 18, 1979

[30] Foreign Application Priority Data

Oct. 18, 1978 [JP] Japan ............................ 53-128767

[51] Int. Cl.³ .......................................... A61B 5/00
[52] U.S. Cl. .................................. 128/777; 433/69
[58] Field of Search ............. 128/721, 733, 774, 776, 128/777, 782; 433/68, 69

[56] References Cited

U.S. PATENT DOCUMENTS

| | | | |
|---|---|---|---|
| 3,239,935 | 3/1966 | Shackelford | 433/69 |
| 3,883,954 | 5/1975 | Simmering et al. | 433/68 |
| 3,955,562 | 5/1976 | Farrar, Jr. | 128/782 |
| 3,983,865 | 10/1976 | Shepard | 128/777 |
| 4,170,225 | 10/1979 | Criglar et al. | 128/733 |

*Primary Examiner*—William E. Kamm

*Attorney, Agent, or Firm*—Koda and Androlia

[57] ABSTRACT

A device for making it possible to visually provide a thorough knowledge of the activities of the masticatory muscles by optically measuring and displaying the EMG potential of the masticatory muscles at the time of matication for use in correcting abnormal and unbalance occlusion patterns. The device comprises a plurality of sets of electrodes (8) and (9) each set consisting of a pair of right and left electrodes, said electrodes being designed to be attached to the surfaces of the masseter and temporal muscles in both sides so as to detect electromyographic potentials in time of mastication, a means (A) for converting the electromyographic potentials detected by said electrodes (8) and (9) respectively into electrical signals for display, a display means (C) for selectively energizing said means (C) in response to the signal, the means (C) including display lines ($L_1$) and ($L_2$) of light-emitting members (12) and (13) which are independent of one another for each of the electrodes (8) and (9). The means (C) is mounted in a position in which a person to be examined (P) is enabled to watch the means (C).

8 Claims, 3 Drawing Figures

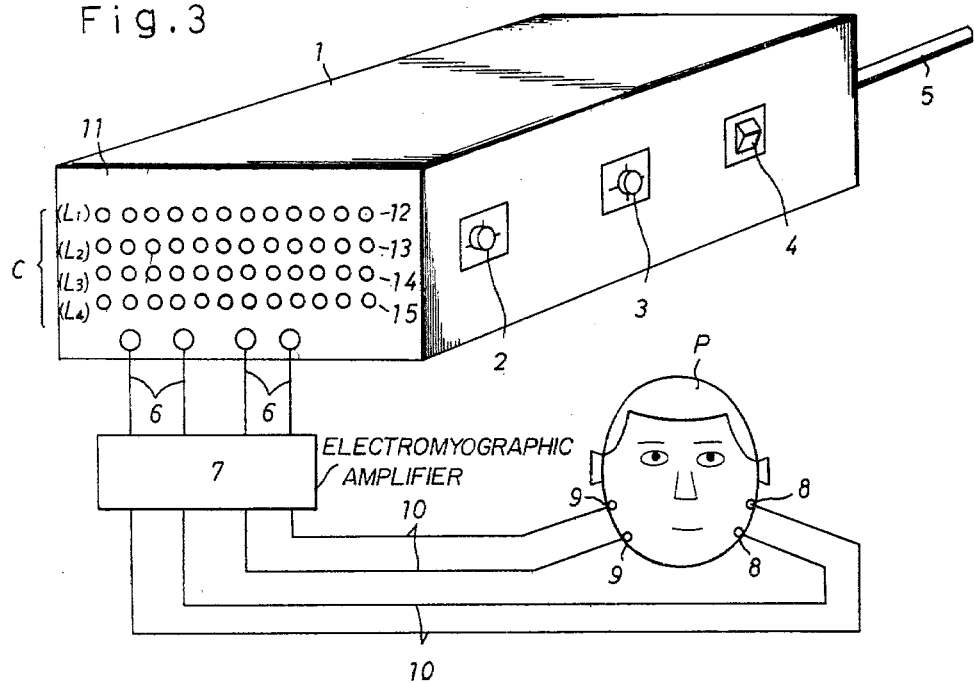

DEVICE FOR DISPLAYING MASTICATORY MUSCLE ACTIVITIES

BACKGROUND OF THE INVENTION

1. Field of the Invention

This invention relates to a device for displaying the masticatory muscle activities and more particularly to a device for making it possible to visually provide a thorough knowledge of the activities of the masticatory muscles by optically measuring and displaying the EMG (electromyographic) potential of the masticatory muscles at the time of mastication.

2. Prior Art

Food taken is masticated by the concerted action of teeth and a so-called group of masticatory muscles such as masseters, temporal muscles, etc. A person wearing prosthetic appliances, especially, a person having a set of full dentures, is apt to have abnormal and unbalanced chearing motions, resulting in fatigue and disorder of the mastication system.

Heretofore, dentists' suggestions and instructions as to how to correct such unbalanced mastication have been given verbally, without satisfactory results.

SUMMARY OF THE INVENTION

Accordingly, it is the primary object of this invention to provide a device that is contributable to the scientific correction of the unbalanced mastication of the kind described through the naked eye of a person to be examined or a patient and through his practice, namely, a device capable of making a person having artificial teeth form a habit of balanced mastication by use of his visual biofeedback mechanism and also capable of physiologically correcting other abnormal occulsion patterns.

In the present invention, EMGs (electromyographics) of masticatory muscles are used as a medium for detecting the coordination pattern of the muscles, and is made visible by converting the medium into light and bringing the light into an optical display. As is well known, the greater the tension produced by the muscles, the greater the above quantity of EMG potential, and the smaller the tension, the smaller the quantity of EMG potential. The present invention is designed in such a manner that the quantity of EMG potential is recognized as a discriminating indication responsive to the quantity of EMG potential. Also, when the coordination pattern of the muscles is viewed in terms of a full mouth, normally, the EMG potential is larger on the mastication-side masseter and smaller on the other side, and in this case, a coordination pattern of EMG potential ideal for concerted working of many muscles is already known. Accordingly, a display of four masticatory muscle activities by the present invention is effective for correctly coordinating the pattern of the individual in comparison of his mastication with this ideal pattern.

DETAILED DESCRIPTION OF THE INVENTION

Figure 1:
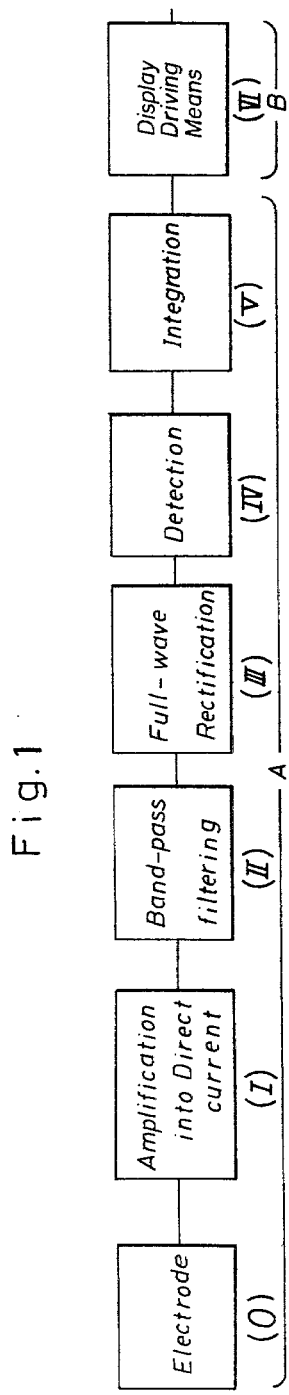
Figure 2:
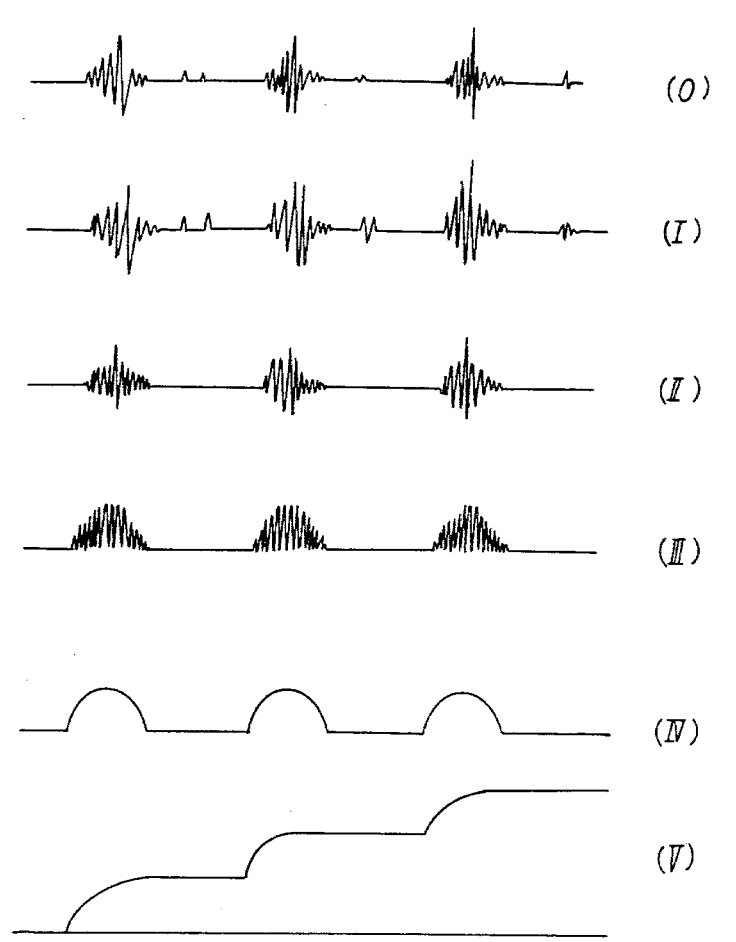

A detailed description will now be given of a preferred embodiment of the present invention with reference to the accompanying drawings, wherein FIG. 1 is an electric block diagram showing how the EMG potential due to occlusion detected by the electrodes is indicated in the form of visible light; FIG. 2 shows wave forms corresponding to each block of FIG. 1; and FIG. 3 shows a schematic diagram explaining the state of the inventive device used.

The device of the present invention is designed to be adapted for general commercial power sources so as to permit its use not only in a dental office but also by people in general at home. In FIG. 3 the numeral 5 designates a power cord to be connected to a commercial power source, and a device body 1 is placed on the table and/or flat surface. The device body 1 is provided in front with display unit 11 which includes a display means C to be later described. An electromygraphic amplifier 7 is connected by circuit cables 6 to the unit 11, and two sets of electrodes 8 and 9, each set consisting of a pair of right and left electrodes in the case shown (namely, four electrodes in all) are connected by circuit cables 10 from the electromyographic amplifier 7. On one side of the device body 1 are mounted a power switch 4, a switch 3 for setting the number of times of mastication, and a changeover switch for amplification factor. The setting switch 3 is a changeover type switch capable of selectively providing desired switch settings to obtain indications of mastication at particular times, continuous mastication for a certain period of time, while the changeover switch 2 permits the selection of the strength of amplification of EMG potential in accordance with each person's difference in masticatory strength. The display means C shown includes light-emitting diodes 12, 13, 14 and 15 (twelve in all), for each line, arranged in a straight line in a manner so that each of the electrodes 8 and 9 may show independently four lines $L_1$, $L_2$, $L_3$ and $L_4$. The electrodes 8, 8 and 9, 9 are attached respectively in pairs to the patient P at two points of masseters and temporal regions, and the EMG potential from there is caught by the electromyographic amplifier 7 an electrical signal and is inputted through cables 6 to an electrical signal conversion means A in the device body 1. The electrical signal outputted by the means A is inputted to a display driving means B and the output from the means B is indicated in the form of discriminating light emission responsive to a quantity of EMG potential. In the embodiment shown, the manner of light emission of the diodes 12 and 13 in each display line $L_1$, $L_2$, $L_3$ and $L_4$ is indicated in the form of a segment of light-emitting line varying in length, depending upon the quantity of EMG potential caught by each of the electrodes 8 and 9. Namely, the strength of occlusion is indicated in terms of the length of a segment of a light-emitting line. The display unit 11 includes the display means C which is placed where the patient P having the electrodes 8 and 9 attached to the masseter and temporal regions can directly watch the unit 11. More specifically, the unit 11 is placed in a location so the patient P is facing it while sitting in a chair. Accordingly, the patient P is able to visually know everything about the state of occulusion on the left and right sides, respectively by the lengths of light-emitting segments of lines $L_1$, $L_2$, and $L_3$, $L_4$, with the result being that the patient P himself can visually practice his intended correction of mastication by watching the display means C. It is optional to select with the switch 3 whether the strength of mastication, in this case, is indicated for each masticatory movement, or for every specified number of time (say, three times) of continous mastication, or for the mean value of a given period of time (say, one minute). When an excess or a deficiency is indicated on the display means C because of differences in the strength of inherent masticatory force between individuals, the excess or deficiency can be suitably adjusted by the changeover switch 2. As described earlier, to compare the light-emitting indication made by the display means C with an ideal occlusion pattern, it is only necessary to have in stock a pattern beforehand copied by the display means C from the ideal occlusion pattern.

Now, a description will be given of electrical and optical procedures taken from the derivation of EMG potential to the light-emitting indication of the potential with reference to FIGS. 1 and 2.

Blocks O through V in FIG. 1 constitute through a chain of the designated blocks a means A for converting myoelectric potential into an electrical signal for display, while blocks O through V in FIG. 2 show wave forms corresponding to the respective blocks O through V in FIG. 1. The EMG potential derived at the electrodes 8 and 9 has been amplified into direct current and has been subjected to band-pass filtering (chiefly a wave form of below 10 Hz and above 600 Hz liable to contain noise component is filtered) and thereafter is converted through full wave rectification, including phase inversion), detection and integration into an indicating signal and is inputted to a driving means B. In the procedure above, each action in the blocks O through V is well known electrically or electronically, and hence a description of such action is omitted. The integral wave form is indicated in the form of three EMG potentials, and it is noted that an indication of a quantity of EMG potential for one masticatory stroke and an indication of the mean quantity of EMG potential for a continuous masticatory movement with a given period of time are different from the wave forms shown in FIG. 2, and that after three EMG potentials in FIG. 2 have been integrated, a description has been omitted of the electric circuit used for clearing the above integration value so that a fourth EMG potential may not be integrated in addition to the integration of the three EMG potentials. The driving means B, in which the well-known IC circuit for energizing light-emitting diodes is used, is designed to select in accordance with output voltage of the integration V the number of diodes to emit light out of a plurality of light-emitting diodes. To explain this fact in conjunction with the display means C, groups of light-emitting diodes 12 and 13 each including twelve diodes respectively placed in display lines $L_1$, $L_2$, $L_3$ and $L_4$ are designed to vary in the number of diodes to emit light in accordance with the quantity of myoelectric potential, and the diodes 12 and 13 which emit light in this case emit light in a straight line series (for example, in such a manner that in $L_1$, six diodes 12 in a series from left to right in the figure and, in line $L_3$, eight diodes 14 emit light), and this straight-line light emitting display is provided in terms of a change in the length of a segment of a line by adjusting the strength of occlusion. In the inventor's opinion, not only is it desirable that the display be as large as possible within the view of the patient P but, also it is proper that empirically the display be one in terms of a segment of a line variable in length. This manner of display, however, is not limited to the embodiment shown but may be one in which a change in the quantity of EMG potential is indicated in terms of a shift of only one diode in the point of light emission (for example, in the manner that only the diode in the fourth place from the left which initially emitted light shifts to the seventh place) and may be concentric, rectangular or otherwise in arrangement, in addition to a straight-line light emitting display. Furthermore, instead of the diodes, use may be made of a liquid crystal display, cathode ray tube display and/or other electro-optical display as the light emitting member. The cost of such displays should also be considered. As the signal conversion means A and conversion means B, selection of conversion means other than the ones illustrated are also within the scope of this invention.

As has already been described so far, the device according to the present invention makes it possible for the patient P to know his own occlusion visually in a feedback state by a display means and accordingly it is of great use to acquire the habit of correcting unbalanced and abnormal occlusion patterns by his own practice, and has proven to be more demonstrative than the oral instruction heretofore practices and brings about a marked increase in the effectiveness of the intended correction.

We claim:

1. A device for displaying masticatory muscle activities for use in correcting unbalanced and abnormal occlusion patterns characterized in that the device comprises a plurality of sets of electrodes (8) and (9) each set consisting of a pair of right and left electrodes, said electrodes being attachable to the surfaces of the masseter and temporal muscles on both sides of a face of a person to be examined so as to detect electromyographic potentials during mastication, a means (I), (II), (III), (IV) and (V) for converting the electromyographic potentials detected by said electrodes (8) and (9) respectively into electrical signals for display, a display means (C), and a means (B) for selectively energizing said display means (C) in response to said signals, said display means (C) comprising display lines ($L_1$), ($L_2$), ($L_3$) and ($L_4$) of light-emitting members (12) and (13) which are independent over one another for each of said electrodes (8) and (9) whereby the masticatory muscle activity can be displayed during a plurality of consecutive occlusions.

2. A device according to claim 1 wherein the display given by said means (C) displays a quantity of electromyographic potential of each muscle.

3. A device according to claim 1, wherein said light-emitting members (12), (13), (14) and (15) are light-emitting diodes.

4. A device according to claim 1 wherein said light-emitting members (12) and (13) are arranged in a straight line for each display line ($L_1$) and ($L_2$) and change in the quantity of EMG potential is displayed in the form of a segment of a line varying in length.

5. A device according to claim 1 wherein said light-emitting members (12) and (13) are arranged in a straight line for each display line ($L_1$) and ($L_2$) and change in quantity of EMG potential is displayed in the form of shift of one light-emitting member alone in the point of light emission.

6. A device according to claim 1, wherein said light-emitting members (12), (13), (14) and (15) are liquid crystal displays.

7. A device for displaying masticatory muscle activity during a plurality of consecutive occlusions for use in correcting unbalanced and abnormal occlusion patterns, said device comprising:
a pair of sets of electrodes, each said set comprising a pair of right and left electrodes, said electrodes further being attachable to facial surfaces of masseter and temporal muscles on both sides of the face of a person to be examined so as to detect electromyographic potential during masication;

an amplifying means for receiving the detected electromyographic potential and for producing an amplified signal;
a band pass filter means for receiving the amplified signal and producing a filtered singal;
a full-wave rectification means for receiving the filtered signal and for producing a full-wave rectifying signal;
a detector means for detecting the amplitude of the rectified signal;
an integration means for receiving and integrating an output of said detector means;
a display means comprising a plurality of display elements; and
a means for selectively energizing said display elements of said display means in response to the magnitude of an output of said integration means.

8. A device for displaying masticatory muscle activity according to claim 7, wherein the band pass of said band pass filter means is 10 to 600 Hz.

* * * * *